United States Patent [19]

Kusano et al.

[11] Patent Number: 5,006,467
[45] Date of Patent: Apr. 9, 1991

[54] CELL CULTURE MICROCARRIERS

[75] Inventors: Hiroshi Kusano, Yokohama; Tsuyoshi Ito, Machida; Hirohisa Kubota, Yokohama, all of Japan

[73] Assignee: Mitsubishi Kasei Corporation, Tokyo, Japan

[21] Appl. No.: 213,251

[22] Filed: Jun. 29, 1988

[30] Foreign Application Priority Data

Jul. 3, 1987 [JP] Japan .................. 62-166712

[51] Int. Cl.$^5$ ............ C12N 11/08; C08F 16/26; C08F 24/00
[52] U.S. Cl. ............... 435/180; 435/240.23; 435/240.24; 435/180; 526/318.4; 526/318.42; 526/336; 526/273; 525/327.3
[58] Field of Search .......... 435/240.24, 240.23, 435/180; 526/318.4, 318.42, 330, 273; 525/327.3

[56] References Cited

U.S. PATENT DOCUMENTS

| | | | |
|---|---|---|---|
| 4,070,348 | 1/1978 | Kraemer | 260/79.3 |
| 4,237,218 | 12/1980 | Monthony et al. | |
| 4,293,645 | 10/1981 | Wovcha et al. | |
| 4,293,654 | 10/1981 | Levine et al. | 435/240.24 |
| 4,352,884 | 10/1982 | Nakashima | 435/120 |
| 4,415,668 | 11/1983 | Siegel | 435/240.24 |
| 4,565,784 | 1/1986 | Franzblau et al. | |
| 4,824,946 | 4/1989 | Schwengers et al. | |

FOREIGN PATENT DOCUMENTS 0066726 12/1982 European Pat. Off. .
74580 4/1986 Japan .
71173 3/1988 Japan .

OTHER PUBLICATIONS

*Develop. Biol. Standard*, vol. 55, pp. 11-23 (S. Karger, Basel, 1984).
*The Proceedings of Biotech Europe '84*, vol. 1, pp. 345-354.
Search Report for European Patent Application 88 110,568.8
*J. Macromol. Sci.-Chem.*, A2(5), pp. 1045-1054, Aug. 1968.
*Biotechnology and Bioengineering*, vol. XXIX, pp. 1155-1163 (1987).
*Chemical Abstracts*, vol. 109, 1988, No. 1, p. 510; #5312g.

*Primary Examiner*—Elizabeth C. Weimar
*Assistant Examiner*—Suzanne Ziska
*Attorney, Agent, or Firm*—Oblon, Spivak, McClelland, Maier & Neustadt

[57] ABSTRACT

Improved cell culture microcarriers are disclosed herein. These improved microcarriers consist of water-insoluble polymer particles constituted by (meth)acrylic ester, characterized in that the particles have an average diameter of 110-1,000 μm and a density of 1.00-1.20 g/ml in a culture medium as well as positively chargeable chemical moieties distributed at least thereon, the moieties being introduced into the particles by the reaction between the ester and ammonia or amine having 5 or less carbon atoms.

3 Claims, No Drawings

CELL CULTURE MICROCARRIERS

BACKGROUND OF THE INVENTION

1. Field of the Invention

This invention relates to cell culture microcarriers for use in the culture of anchorage-dependent cells, particularly to cell culture microcarriers suitable for use in high-density cultivation of the anchorage-dependent cells attached to the suspended or stationary microcarriers.

2. Description of the Prior Art

In recent years, a rapid progress had been made in the culture of anchorage-dependent cells. One of the previous operational techniques employed therefor is a microcarrier system. The microcarriers which have been reported to date are, for example, those formed from a cross-linked dextran matrix such as Cytodex ® (commercially available from Pharmacia Fine Chemicals, Inc.,) and Superbeads (commercially available from Flow Labs, Inc.,), and those formed from cellulose particles such as DE-52 and DE-53 (commercially available from Whatman, Inc.,). However, these microcarriers have a disadvantage that the recovery of desired biologically active substances is very low to an extremely hydrophobic interaction with proteins of diethylaminoethyl (DEAE) groups used therein as functional groups.

Although microcarriers based on polystyrene are also available, they have the same disadvantage as mentioned above because polystylene itself is highly hydrophobic substance.

If base polymers or functional groups having a higher hydrophobicity were used, distensibility or growability of cells would be deleteriously effected in a low serum condition, which might even lead to death of the cells.

An aspect of the present invention is to provide cell culture microcarriers which can be produced economically.

Another aspect of the present invention is to provide cell culture microcarriers having a low non-specific absorbing property for proteins and being capable of effectively recovering desired biologically active substances produced by animal cells.

A further aspect of the present invention is to provide cell culture microcarriers which can be used in a low serum condition.

Thus, the cell culture microcarriers according to the present invention consist of water-insoluble polymer particles constituted by (meth)acrylic ester, the particles having an average diameter of 100–1,000 μm and a density of 1.00–1.20 g/ml in a culture medium as well as positively chargeable chemical moieties distributed at least on their surfaces, the moieties being introduced thereinto by the reaction between the above ester and ammonia or amine having 5 or less carbon atoms.

DETAILED DESCRIPTION OF THE INVENTION

The essential advantages of the present invention may be derived from the characteristics that a base matrix of the microcarriers according to the present invention consists of the water-insoluble particles obtained by the polymerization of (meth)acrylic ester and that the positively chargeable chemical moieties are introduced into the particles by the reaction between the ester and ammonia or amine having 5 or less carbon atoms.

The microcarriers according to the present invention may be prepared by producing the water-insoluble polymer particles by O/W or W/O/W type suspension polymerization using (meth)acrylic ester as a monomer followed by treating the resulting polymer particles with ammonia or amine having 5 or less carbon atoms.

As the (meth)acrylic ester suitable for use in the present invention, there may be exemplified 2-hydroxyethyl (meth)acrylate, diethyleneglycol (meth)acrylate, octaethyleneglycol (meth)acrylate, polyethyleneglycol (meth)acrylate, methyl (meth)acrylate, ethyl (meth)acrylate and glycidyl (meth)acrylate. Any suitable cross-linking agent may be optionally added to the above ester monomers. The polymer particles constituted by polyethyleneglycol (meth)acrylate and/or glycidyl (meth)acrylate preferably contain the cross-linking agent in order to prevent the leakage of the (meth)acrylic ester from the produced particles unless they are water-insoluble. Any compound which can be co-polymerized with polyethyleneglycol (meth)acrylate and/or glycidyl (meth)acrylate may be used as the cross-linking agent, examples of which are ethyleneglycol dimethacrylate, diethyleneglycol dimethacrylate, polyethyleneglycol dimethacrylate, glycerol dimethacrylate and glycerol trimethacrylate.

Although the addition of the cross-linking agent is preferable in view of the above, a high content thereof would reduce a swelling level of the polymer particles and make it impossible to obtain a preferred density. Accordingly, the content of the cross-linking agent preferably ranges from 0 to 100%, more preferably from 0 to 40% by weight.

2-Hydroxyethyl (meth)acrylate, polyethyleneglycol (meth)acrylate, glycidyl (meth)acrylate and the like may be advantageously used in the present invention because they can economically produce the hydrophilic polymer particles.

The suspension polymerization of O/W or W/O/W type according to the present invention may be performed in a conventional manner in the presence of an organic diluent and polymerization initiator.

Any organic diluent which is inactive to functional groups such as glycidyl and hydroxyl may be used for the polymerization. Examples of suitable organic diluents include pentanol, hexanol, heptanol, octanol, cyclohexanol, toluene, chlorobenzene, dibutylether, diamylether, propyl acetate, butyl acetate, methylisobutylketone and cyclohexanone. The organic diluents may be preferably added in 0–10.0 times by weight the total amount of monomers.

Examples of suitable polymerization initiators include benzoyl peroxide, lauroyl peroxide and azobisisovaleronitrile, which may be usually used in an amount of from 0.01 to 5%, preferably from 0.05 to 1.0% by weight of the total monomers.

The average diameter and density of the cell culture microcarriers according to the present invention may depend to the composition of the monomers and the ratio of the cross-linking and organic diluent used, the type of the positively chargeable chemical moieties, the stirring rate during the polymerization and the shape or form of a stirring propeller. The former and latter should be, however, preferably adjusted to the ranges of from 100 to 1,000 μm and of from 1.00 to 1.20 g/ml, respectively, in order to keep the microcarriers homogeneously suspended under stirring or in a flowing station air-lift or up-flow type) during cultivation. Furthermore, the microcarriers preferably have a narrow distribution in diameter for the purpose of effecting the homogeneous attachment and growth of cells as well as the homogeneous suspension of the microcarriers.

Upon the completion of the suspension polymerization, the resulting polymer particles are filter off and washed.

The existence of the positively chargeable chemical moieties at least one the surface of the microcarriers is inevitably required so that the anchorage-dependent cells may be advantageously attached to and grow on the microcarriers. The inventors have already proposed cell culture microcarriers which have positive charable chemical moieties (cf. Japanese Patent Application No. 217610/86).

As previously described, it has now been discovered that ammonia and amine having 5 or less carbon atoms may be advantageously employed as the above positively chargeable chemical moeities by the following reasons: they can effectively attach anchorage-dependent cells to the microcarriers and proliferate them even with a low serum concentration; they hardly adsorb the desired biologically active substances which were produced by animal cells, or alternatively they can efficiently elute the desired substances which have been once adsorbed thereto.

As the number of carbon atoms in amine (hydrophobic parameter) becomes higher, the interaction between the cells and the microcarriers becomes stronger, which will usually result in the increase of the number of the attached cells to the microcarriers, but will also make it difficult to elute the biologically active substances once adsorbed by the microcarriers. Too many carbon atoms in amine would even inhibit the growth and spread of the cells.

Examples of preferred positively chargeable chemical moieties according to the present invention include ammonia, methylamine, dimethylamine, trimethylamine, ethylamine, diethylamine, butylamine, dimethylhydrazine, ethylenediamine, 1,3-propanediamine, 1,4-butanediamine, N,N-dimethylethylenediamine, ethanolamine, N-methylethanolamine, 2-hydroxypropylamine, 3-amino-1,2-propanediol, methoxyethylamine, glycolamine($NH_2$—$CH_2$—$CH_2$—O—$CH_2$—$CH_2$—OH), 2-(2-aminoethylamino)ethanol($NH_2$—$CH_2$—$CH_2$—NH—$CH_2$—$CH_2$—OH), 3-methoxypropylamine, 2-ethoxyethylamine, 2-amino-2-methyl-1-propanol, dimethylethanolamine, 2-methyl-2-amino-1,3-propanediol, N-methyldiethanolamine, 2-(2-aminoethylamino)ethanol, aminoethanethiol, piperazine, pyrrolidine, imidazolidine, pyrazolidine, morpholine, thiamorpholine, diethylenetriamine, dimethylaminoethyl halide and dimethylaminoethanol.

The above-mentioned chemical moieties may be reacted with a functional group such as the terminal hydroxy group of ethylenglycol (meth)acrylate, diethyleneglycol (meth)acrylate and polyethyleneglycol (meth)acrylate which have been beforehand activated by bromocyan, carbonyl imidazole or 2,2,2-trifluoroethanesulfonyl chloride. Alkylamine, alkylenediamine and alkanolamine may be easily introduced into the polymer particles made of glycidyl (meth)acrylate through the reaction in the presence of a suitable solvent such as water, ethanol and dioxane for a few hours at a temperature ranging from a room temperature to a refluxing point with the epoxy or glyceryl group generated therefrom by hydrolysis. The positively chargeable chemical moieties may be also formed through the reaction of hydroxy groups of the polymer particles with dialkylaminoalkyl chloride, dialkylaminoalkyl bromide, trialkylaminoalkyl chloride and trialkylaminoalkyl bromide.

In view of the aspects of the present invention, it is at least required that the positively chargeable chemical moieties should be distributed on the particle surfaces (about 10 nm in depth) which may be in contact with cells. The chemical moieties may, however, be present inside or throughout the polymer particles without causing any deleterious effects.

The content of the positively chargeable chemical moeities may vary with such factors as the cells and the chemical moeities themselves, the concentration of microcarriers in culture medium and the culture conditions. The charge capacity found suitable ranges between 0.5 and 2.5 meg per one gram of dry microcarriers.

The invention is further illustrated by the following examples, which may not be construed as limiting the scope of this invention.

EXAMPLE 1

Into a four-necked flask (300 ml) equipped with a thermometer, $N_2$ duct, condenser and stirring blades, 30 g of $CaCl_2$ dihydrate, 50 ml of an aqueous polyvinyl alcohol solution and 85 ml of ion-exchanged water were added and mixed. The following reactions were all performed in $N_2$ atmosphere. To the resulting solution were added 30 g of 1-hexanol, 30 g of cyclohexanol, 15 g of 1-octanol, 13 g of polyethyleneglycol methacrylate (PE-60: trade name, commercially available from Nippon Oil and Fats Co., Ltd.), 6.0 g of glycidyl methacrylate, 1.00 g of gylcerol dimethacrylate and 200 mg of azobisisovaleronitrile (V-65, trade name). After gradually heated to 70° C., the polymerization reaction was carried out for 5 hours while keeping that temperature. Upon the completion of the reaction, the resulting polymer was filtered off on Buchner funnel and washed. The washed polymer was again taken into the flask, to which a certain amount of methanol was added and boiled under stirring for 20 min. so as to wash the polymer. The above washing procedures was repeated 6 times. The polymer was again washed with water on Buchner funnel and then in the flask under stirring for about 30 min. at about 90° C., which washing procedure was repeated again.

The colorless and transparent particles having a spherical body thus produced with a yield of 84% were passed through a standard sieve to select the particles of from 210 to 250 μm in diameter, which are referred to hereinafter as "Polymer 1".

Polymer 1 (30 ml when settled in a messcylinder) was thoroughly washed and allowed to swell with 1,4-dioxane. The swollen polymer 1 and 30 ml of 1,4-dioxane were added to a 300 ml flask. To this was added dropwise 15 ml of dioxane solution containing 5.0 g of methoxyethanolamine and reacted for 4 hours at 70° C. The polymer particles thus prepared were sufficiently washed with water and with 10% sulfuric acid aqueous solution successively. The washed particles and fresh 10% sulfuric acid aqueous solution of 50 ml were taken again into the flask and heated for 4 hours at 70° C. to hydrolyze unreacted epoxy groups, followed by a thorough washing. The resulting polymer particles are designed at "Micro Carrier-1(MC-1)". The elemental analysis of MC-1 is as follows:

| C | H | N |
|---|---|---|
| 53.26% | 8.23% | 1.94% |

Based on the above analysis the charge capacity of MC-1 was characterized to be 1.54 meq per gram of dry. The degree of swelling in phosphate-buffered saline solution (PBS), average diameter and density of MC-1 were measured to be 12.5 ml/g-gel, 210 μm and 1.05 g/ml, respectively.

EXAMPLE 2

Polymer 1 (30 ml when settled in a messcylinder) was thoroughly washed and allowed to swell with 1,4-dioxane. The swollen polymer 1 and 30 ml of 1,4-dioxane were added to a 300 ml flask. To this was added dropwise 15 ml of dioxane solution containing 5.0 g of ethanolamine. The same procedures as in Example 1 were carried out to yield "Micro Carriers 2 (MC-2)", the elemental analysis of which is as follows:

| C | H | N |
|---|---|---|
| 47.26% | 8.00% | 2.14% |

Based on the above analysis the charge capacity of MC-2 was characterized to be 1.69 meq per gram of dry. The degree of swelling in PBS, average diameter and density of MC-2 were measured to be 23.3 ml/g-gel, 210 μm and 1.03 g/ml, respectively.

EXAMPLE 3

Polymer 1 (30 ml when settled in a messcylinder) was thoroughly washed and allowed to swell with 1,4-dioxane. The swollen polymer 1 and 30 ml of 1,4-dioxane were added to a 300 ml flask. To this was added dropwise 15 ml of dioxane solution containing 5.0 g of aminoethanethiol. The same procedures as in Example 1 were carried out to yield "Micro Carriers 3 (MC-3)", the elemental analysis of which is as follows:

| C | H | N |
|---|---|---|
| 52.71% | 8.10% | 2.23% |

Based on the above analysis the charge capacity of MC-3 was characterized to be 1.52 meq per gram of dry. The degree of swelling in PBS, average diameter and density of MC-3 were measured to be 17.9 ml/g-gel, 190 μm and 1.04 g/ml, respectively.

EXAMPLE 4

Polymer 1 (30 ml when settled in a messcylinder) was thoroughly washed and allowed to swell with 1,4-dioxane. The swollen polymer 1 and 30 ml of 1,4-dioxane were added to a 300 ml flask. To this was added dropwise 15 ml of dioxane solution containing 7.5 g of diglycolamine. The same procedures as in Example 1 were carried out to yield "Micro Carriers 4 (MC-4)", the elemental analysis of which is as follows:

| C | H | N |
|---|---|---|
| 47.26% | 8.00% | 2.14% |

Based on the above analysis the charge capacity of MC-4 was characterized to be 1.52 meq per gram to dry. The degree of swelling in PBS, average diameter and density of MC-4 were measured to be 22.6 ml/g-gel, 215 μm and 1.03 g/ml, respectively.

EXAMPLE 5

Polymer 1 (30 ml when settled in a messcylinder) was thoroughly washed and allowed to swell with 1,4-dioxane. The swollen polymer 1 and 30 ml of 1,4-dioxane were added to a 300 ml flask. To this was added dropwise 15 ml of 50 percent dioxane solution containing 5.0 g of 2,3-dihydroxypropylamine. The same procedures as in Example 1 were carried out to yield "Micro Carriers 5 (MC-5)", the elemental analysis of which is as follows:

| C | H | N |
|---|---|---|
| 51.48% | 8.03% | 1.80% |

Based on the above analysis of charge capacity of MC-5 was characterized to be 1.45 meq per gram of dry. The degree of swelling in PBS, average diameter and density of MC-5 were measured to be 21.3 ml/g-gel, 210 μm and 1.03 g/ml, respectively.

EXAMPLE 6

Polymer 1 (30 ml when settled in a messcylinder) was thoroughly washed and allowed to swell with 1,4-dioxane. The swollen polymer 1 and 30 ml of 1,4-dioxane were added to a 300 ml flask. To this was added dropwise 5.0 ml of 28% ammoric aqueous mixture was gradually heated to and solution and the reaction kept at 40° C. during the reaction. The reaction was continued for 4 hours while adding 3.0 ml of 28% ammonia at intervals of one hour. The same procedures as in Example 1 were carried out to yield "Micro Carriers 6 (MC-6)", the elemental analysis of which is as follows:

| C | H | N |
|---|---|---|
| 52.12% | 8.24% | 1.36% |

Based on the above analysis the charge capacity of MC-6 was characterized to be 1.62 meq per gram of dry. The degree of swelling in PBS, average diameter and density of MC-6 were measured to be 21.5 ml/g-gel, 210 μm and 1.03 g/ml, respectively.

REFERENCE EXAMPLE

Polymer 1 (30 ml when settled in a messcylinder) was thoroughly washed and allowed to swell with 1,4-dioxane. The swollen polymer 1 and 30 ml of 1,4-dioxane were added to a 300 ml flask. To this was added dropwise 15 ml of dioxane solution containing 10.0 g of 1,6-hexanediamine. The same procedures as in Example 1 were carried out to yield "Micro Carriers 7 (MC-7)", the elemental analysis of which is as follows:

| C | H | N |
|---|---|---|
| 51.34% | 8.51% | 3.47% |

Based on the above analysis the charge capacity of MC-7 was characterized to be 1.45 meq per gram of dry. The degree of swelling in PBS, average diameter and density of MC-7 were measured to be 18.1 ml/g-gel, 205 μm and 1.04 g/ml, respectively.

EXAMPLE 7

The adsorbing properties of the microcarriers prepared in the above Examples were determined using bovine serum albumin (BSA) as a standard protein sample.

The microcarriers were allowed to swell in PBS, pH 7.40 to give 10.0 ml. The swollen microcarriers were dewatered and added to 100 ml of PBS containing 0.10% BSA followed by stirring for 6 hours at 37° C. The absorbing properties of the microcarriers were determined by measuring the absorbance (280 nm) of each PBS suspension. The results are shown in Table 1 below.

TABLE 1

| EXAMPLE No. | Microcarriers | Adsorption ratio (%) |
|---|---|---|
| EXAMPLE 1 | MC-1 | 0 |
| EXAMPLE 2 | MC-2 | 0 |
| EXAMPLE 3 | MC-3 | 0.6 |
| EXAMPLE 4 | MC-7 | 0 |
| EXAMPLE 5 | MC-5 | 0 |
| EXAMPLE 6 | MC-6 | 0 |
| REFERENCE EXAMPLE 1 | MC-7 | 98.1 |
| REFERENCE EXAMPLE 2 | Cytodox ® (Pharmacia) | 6.2 |

EXAMPLE 8

Vero cells (African green monkey's renal calls), CHO-K$_1$ cells (Chinese Hamster Ovary) cells and L-929 cells (mouse cellulofibroblast) were subjected to cultivationusing the cell culture microcarriers according to the present invention.

MC-1, MC-2, MC-3, MC-4, MC-5, MC-6 and Cytodex-1 were thoroughly washed with water and Dulbecco's Modified Eagle's Medium successively. The resulting microcarriers (30 ml) were autoclaved for 20 min. at 120° C. The microcarriers thus sterilized and 15 ml of fetal calf serum were added to a spinner flask and TS-2 medium was supplemented up to 300 ml of a total volume. Microcarriers cultures were initiated by adding a suspension containing $3.0-5.0 \times 10^7$ trypsinized cells to the above microcarriers suspension. L-929 cells and Vero cells had reached a confluent state in about 6-8 days while CHO-K$_1$ cells required about 8-11 days to reach the confluent state. The cultures of these cells were continued thereafter in a serum-free condition.

What is claimed is:

1. Mammalian anchorage-dependent cell culture microcarriers consisting of water-insoluble polymer particles, charcterized in that the particles are constituted by polyethyleneglycol (meth)acrylate, glycidyl (meth)acrylate and a cross linking agent, and have an average diameter of 100–1,000 μm and a density of 1.00–1.20 g/ml in a culture medium as well as positively chargeable chemical moieties distributed at least on their surfaces, the moieties being introduced into the particles by a reaction between glycidyl (meth)acrylate and ammonia or an amine having 5 or less carbon atoms and being bonded thereto directly through a nitrogen atom.

2. Cell culture microcarriers according to claim 1, wherein the charge capacity is adjusted to the range of between 0.5 and 2.5 meq per gram dry.

3. Mammalian anchorage-dependent cell culture microcarriers of claim 1 having mammalian cells attached thereto.

* * * * *